United States Patent
Peitz et al.

(10) Patent No.: US 11,254,625 B2
(45) Date of Patent: Feb. 22, 2022

(54) PROCESS FOR INHIBITING OLIGOMERIZATION OF C3- TO C5-OLEFINS

(71) Applicant: Evonik Operations GmbH, Essen (DE)

(72) Inventors: Stephan Peitz, Oer-Erkenschwick (DE); Guido Stochniol, Haltern am See (DE); Reiner Bukohl, Marl (DE); Helene Reeker, Dortmund (DE); Niklas Paul, Marl (DE)

(73) Assignee: Evonik Operations GmbH, Essen (DE)

( * ) Notice: Subject to any disclaimer, the term of this patent is extended or adjusted under 35 U.S.C. 154(b) by 161 days.

(21) Appl. No.: 15/929,599

(22) Filed: May 12, 2020

(65) Prior Publication Data
US 2020/0361834 A1 Nov. 19, 2020

(30) Foreign Application Priority Data
May 14, 2019 (EP) .................................... 19174290

(51) Int. Cl.
*C07C 2/10* (2006.01)
*B01J 23/78* (2006.01)

(52) U.S. Cl.
CPC .................. *C07C 2/10* (2013.01); *B01J 23/78* (2013.01); *C07C 2521/04* (2013.01); *C07C 2521/08* (2013.01); *C07C 2523/04* (2013.01); *C07C 2523/755* (2013.01)

(58) Field of Classification Search
CPC ... C07C 2/10; C07C 2521/04; C07C 2521/08; C07C 2523/04; C07C 2523/755; C07C 2521/12; C07C 2/08; B01J 23/78; C10G 50/00
See application file for complete search history.

(56) References Cited

U.S. PATENT DOCUMENTS

| | | | |
|---|---|---|---|
| 7,161,054 B2 | 1/2007 | Heidemann et al. | |
| 9,682,898 B2 | 6/2017 | Peitz et al. | |
| 2006/0217580 A1* | 9/2006 | Kuechler | C09K 8/32 585/533 |
| 2014/0135554 A1* | 5/2014 | Nicholas | C07C 2/12 585/533 |
| 2014/0135555 A1* | 5/2014 | Nicholas | C07C 2/12 585/533 |
| 2015/0376083 A1* | 12/2015 | Mehlberg | C07C 5/333 585/255 |
| 2016/0137934 A1* | 5/2016 | Luebke | C10G 69/126 585/255 |

FOREIGN PATENT DOCUMENTS

| | | |
|---|---|---|
| EP | 1 457 475 | 9/2004 |
| WO | 2014/207034 | 12/2014 |

OTHER PUBLICATIONS

U.S. Appl. No. 15/929,599, filed May 12, 2020, Stochniol et al.

* cited by examiner

*Primary Examiner* — Ali Z Fadhel
(74) *Attorney, Agent, or Firm* — Grüneberg and Myers PLLC

(57) ABSTRACT

Oligomerization of $C_3$- to $C_5$-olefins using a catalyst is inhibited, wherein the oligomerization is carried out in at least one reaction stage including at least one reactor and at least one distillation column, and wherein the oligomer content in the feed stream to the at least one reactor of the at least one reaction stage is at least 1% by weight.

20 Claims, No Drawings

PROCESS FOR INHIBITING OLIGOMERIZATION OF C3- TO C5-OLEFINS

CROSS-REFERENCE TO RELATED APPLICATION

The present application claims the benefit to European application EP 19174290.7, filed on May 14, 2019, the content of which is hereby incorporated by reference in its entirety.

BACKGROUND OF THE INVENTION

Field of the Invention

The present invention relates to a process for inhibiting oligomerization of $C_3$- to $C_5$-olefins using a catalyst, wherein the oligomerization is carried out in at least one reaction stage comprising at least one reactor and at least one distillation column and wherein the oligomer content in the feed stream to the at least one reactor of the at least one reaction stage is at least 1% by weight.

Discussion of the Background

Oligomerization is generally understood as meaning the reaction of unsaturated hydrocarbons with themselves to form correspondingly longer-chain hydrocarbons, the so-called oligomers. For instance, an olefin having six carbon atoms (hexene) can be formed by oligomerization of two olefins having three carbon atoms (propene). The oligomerization of two molecules with one another is also referred to as dimerization.

The resulting oligomers are intermediates that are used, for example, for producing aldehydes, carboxylic acids, and alcohols. The oligomerization of olefins is carried out on a large industrial scale either in the homogeneous phase using a dissolved catalyst or heterogeneously over a solid catalyst, or else with a two-phase catalyst system.

Processes for oligomerizing olefins are sufficiently well known in the related art and are used on an industrial scale. The production quantities amount to several thousand kilotons per year in Germany alone. The source of the olefins for the oligomerization processes are generally olefin-containing fractions from cracking processes (for example steam crackers or fluid catalytic crackers) which, in addition to the olefins, also comprise corresponding alkanes.

In technical oligomerization processes, high reaction rates of the olefins involved can occur during operation due to various effects that may arise. These high reaction rates can occur across the entire reactor or only locally, that is to say at spatially limited locations in the reactor. Since the oligomerization reaction is an exothermic reaction, reaction rates which are too high can also lead to a self-accelerating reaction which may be accompanied by undesired by-product formation, the occurrence of cracking reactions, destruction of the catalyst, increased heat generation (locally or over the entire reactor) and inadmissible excess pressures until the product is discharged.

The object of the present invention was therefore to provide a process by means of which art oligomerization reaction of $C_3$- to $C_5$-olefins can be specifically inhibited in order to minimize or completely prevent negative effects of any locally increased reaction rates.

SUMMARY OF THE INVENTION

The present invention includes the following embodiments:

1. Process for the specific inhibition of oligomerization of $C_3$- to $C_5$-olefins, wherein the oligomerization is carried out with a feed mixture comprising the $C_3$- to $C_5$-olefins, using a heterogeneous oligomerization catalyst in at least one reaction stage, the at least one reaction stage in each case comprising at least one reactor in which the oligomerization of the olefins is carried out to form an oligomerizate, and at least one distillation column in which the oligomers formed in the oligomerization are at least partially separated from the residual oligomerizate, characterized in that
   the oligomerization is inhibited by the fact that the content of oligomers in the feed to the at least one reactor of the at least one reaction stage, which consists of recycled residual oligomerizate and the fresh feed of the feed mixture, is at least 1% by weight, based on the total composition of the feed, with the proviso that
   the inhibition is carried out only when a predetermined threshold value of a process or plant parameter is exceeded, which indicates that the reaction rate of the oligomerization is too high, at least locally, i.e. above a predetermined threshold value, in one or more reactors, based on the respective reactor.
2. Process according to embodiment 1, wherein the content of oligomers in the feed to at least one reactor of the at least one reaction stage is 1% by weight to 10% by weight based on the total composition of the feed.
3. Process according to embodiment 1 and 2, wherein the heterogeneous oligomerization catalyst is a transition metal-containing oligomerization catalyst comprising a transition metal compound and a support material, preferably an aluminosilicate support material.
4. Process according to embodiment 3, wherein the heterogeneous oligomerization catalyst has a composition of 1.5 to 40% by weight NiO, 5 to 30% by weight $Al_2O_3$, 55 to 80% by weight $SiO_2$ and 0.01 to 2.5% by weight of an alkali metal oxide.
5. Process according to any of embodiments 1 to 4, wherein the oligomerization in each of the reaction stages present is carried out at a temperature in the range of 50 to 200° C., preferably 60 to 180° C., particularly preferably in the range of 60 to 130° C.
6. Process according to any of embodiments 1 to 5, wherein the pressure in the oligomerization in each of the reaction stages present is from 10 to 70 bar, preferably from 20 to 55 bar.
7. Process according to any of embodiments 1 to 6, wherein $C_4$-olefins are used in the process.
8. Process according to any of embodiments 1 to 7, wherein the process or plant parameter which indicates that the reaction rate is too high when a predetermined threshold value is exceeded is the temperature increase, the absolute or local temperature in the reactor, the concentration of the products and/or the by-products, the pressure increase due to the increasing vapour pressure at elevated temperature or the pressure loss across the reactor.
9. Process for the oligomerization of $C_3$- to $C_5$-olefins, wherein the oligomerization is carried out with a feed mixture comprising the $C_3$- to $C_5$-olefins, using an oligomerization catalyst in at least one reaction stage to obtain an oligomerizate, wherein the oligomers formed are separated at least partially in at least one downstream distillation column from the residual oligomerizate, which is at least partially recycled to the at least one reactor and characterized in that the reaction stage or at least one of the reaction stages comprises at least one adiabatically operated reactor, wherein in the adiabatically operated reactor a temperature increase, i.e. the difference between the temperature of the reactor discharge and the temperature of the reactor feed, is at least temporarily 40 K or more, and that the temperature increase is monitored and when the temperature increase exceeds a threshold value of 40 K, the oligomer content in the feed to the at least one reactor of the at least one reaction stage, which consists of recycled residual oligomerizate and the fresh feed of the feed mixture, is adjusted to 1% by weight to 10% by weight, based on the total composition of the feed.

10. Process according to embodiment 9, wherein the heterogeneous oligomerization catalyst is a transition metal-containing oligomerization catalyst comprising a transition metal compound and a support material, preferably an aluminosilicate support material.

11. Process according to embodiment 10, wherein the heterogeneous oligomerization catalyst has a composition of 15 to 40% by weight NiO, 5 to 30% by weight $Al_2O_3$, 55 to 80% by weight $SiO_2$ and 0.01 to 2.5% by weight of an alkali metal oxide.

12. Process according to any of embodiments 9 to 11, wherein the oligomerization in each of the reaction stages present is carried out at a temperature in the range of 50 to 200° C., preferably 60 to 180° C., particularly preferably in the range of 60 to 130° C.

13. Process according to any of embodiments 9 to 12, wherein the pressure in the oligomerization in each of the reaction stages present is from 10 to 70 bar, preferably from 20 to 55 bar.

14. Process according to any of embodiments 9 to 13, wherein $C_4$-olefins are used in the process.

DETAILED DESCRIPTION OF THE INVENTION

It was surprisingly found that the negative effects described (increase in the reaction rate, increased heat generation, increased by-product formation) occur precisely when the oligomers are adequately separated from the residual oligomerizate, which is recycled to the reactor. In contrast, if the content of oligomers in the feed to the at least one reactor of the at least one reaction stage, which consists of the recycled residual oligomerizate and the fresh feed of the feed mixture used, is increased, the negative effects do not occur or can be reduced. The underlying object could therefore be achieved in accordance with the present invention in that the content of oligomers in the feed to the at least one reactor of the at least one reaction stage, which consists of recycled residual oligomerizate and the fresh feed of the feed mixture, is at least 1% by weight, based on the total composition of the feed. This is reproduced in embodiment 1. Preferred embodiments of the process are specified below.

The process according to the invention is a process for inhibiting oligomerization of $C_3$- to $C_5$-olefins, preferably $C_4$-olefins, wherein the oligomerization is carried out with a feed mixture comprising $C_3$- to $C_5$-olefins, preferably $C_4$-olefins, using an oligomerization catalyst in at least one reaction stage, the at least one reaction stage in each case comprising at least one reactor in which the oligomerization of the olefins is carried out to form an oligomerizate, and at least one distillation column in which the oligomers formed in the oligomerization are at least partially separated from the residual oligomerizate, characterized in that the content of oligomers in the feed to the at least one reactor of the at least one reaction stage, which consists of recycled residual oligomerizate and fresh feed of the feed mixture, is at least 1% by weight, preferably 1% by weight to 10% by weight, more preferably 1% by weight to 5% by weight, particularly preferably 1% by weight to 3% by weight, based on the total composition of the feed, with the proviso that the inhibition is carried out only when a predetermined threshold value of a process or plant parameter is exceeded, which indicates that the reaction rate of the oligomerization is too high, at least locally, i.e. above a predetermined threshold value of the reaction rate, in one or more reactors, based on the respective reactor.

Accordingly, the process according to the invention relates to a process for the oligomerization of $C_3$- to $C_5$-olefins, preferably $C_4$-olefins, which is known per se, which is inhibited by recycling or supplying increased amounts of oligomers (increased compared to normal oligomerization processes). However, the inhibition according to the invention is carried out only when a predetermined threshold value of a process or plant parameter is exceeded, which indicates that the reaction rate is too high, at least locally (in relation to the respective reactor), in one or more reactors. The process or plant parameter that indicates an excessively high reaction rate when a predetermined threshold value is exceeded can be, for example, the temperature rise (difference between the temperature of the reactor discharge and the temperature of the reactor feed), the absolute or local temperature in the reactor, the concentration of the products and/or of the by-products, the increase in pressure caused by the increasing vapour pressure at elevated temperature or the pressure loss across the reactor (e.g. due to a gas phase forming).

The selection of the most suitable parameter for monitoring the reaction rate is dependent on various factors, for example the design of the plant or the temperature control of the reactors. With respect to the temperature control, the reactors used in the process according to the invention can be operated isothermally or adiabatically. The reactors in one or in all reaction stages can be operated in the same manner. However, it is also possible in the process according to the invention that reactors operated both isothermally and adiabatically are present in one or all reaction stages. In the context of the present invention, adiabatically operated means that the reactor is not operated isothermally but a temperature increase of >10K is allowed.

In one embodiment, in which the reaction stage or at least one of the reaction stages comprises at least one adiabatically driven reactor, the temperature rise is monitored, a maximum temperature rise of 40 K being the threshold value. Above this, at least locally increased reaction rates are to be expected, due to the temperature, especially at temperatures in the reactor feed of 60° C. or more. In addition, the temperature of the product mixture withdrawn from the reactor can be too high for the downstream process steps. The maximum temperature inside the reactor or the reactor feed at the existing pressure is accordingly preferably lower than the boiling temperature of the feed olefins used. The corresponding temperature-pressure pairings for the boiling points of the hydrocarbon mixtures that can be used are familiar to those skilled in the art.

Accordingly, in principle a classic oligomerization process is initially carried out, in which a parameter is monitored and in which, if a predetermined threshold value of the parameter is exceeded, the method according to the invention for inhibition is carried out such that the amount of oligomers in the feed stream to the reactor is adjusted to at least 1% by weight in order to achieve the desired inhibition. If the inhibition is successful, the amount of oligomers in the feed stream to the reactor can be set to the previous value or the inhibition according to the invention can be ended. This can be done manually or automatically, for example computer-controlled. The amount of oligomers in the feed stream is preferably adjusted to at least 1% by weight until the parameter is again below the previously determined threshold value, i.e. only temporarily. The process is then continued again under the usual production conditions.

The present invention therefore further relates to a process for the oligomerization of $C_3$- to $C_5$-olefins, preferably $C_4$-olefins, wherein the oligomerization is carried out with a feed mixture comprising $C_3$- to $C_5$-olefins, preferably $C_4$-olefins, using an oligomerization catalyst in at least one reaction stage to obtain an oligomerizate, wherein the oligomers formed are separated at least partially in at least one downstream distillation column from the residual oligomerizate, which is at least partially recycled to the at least one reactor, characterized in that the reaction stage or at least one of the reaction stages comprises at least one adiabatically operated reactor, wherein in the adiabatically operated reactor a temperature increase, i.e. the difference between the temperature in the reactor discharge and the temperature in the reactor feed (T in the reactor discharge−T in the reactor feed) is 40 K or more at least temporarily, and in that the temperature increase is monitored and when the temperature increase exceeds a threshold value of 40 K, the oligomer content in the feed to the at least one reactor of the at least one reaction stage, which consists of recycled residual oligomerizate and fresh teed of the feed mixture, is adjusted to 1% by weight to 10% by weight, preferably 1% by weight to 5% by weight, particularly preferably 1% by weight to 3% by weight, based on the total composition of the feed.

The temperature increase is monitored accordingly, particularly by measuring the temperature at the inlet and outlet of the reactor. Suitable measuring devices are known to those skilled in the art. The temperature increase can then be determined from the two values by simple subtraction. The monitoring can be carried out continuously or discontinuously, i.e. by measurement at certain time intervals, for example at intervals of seconds, minutes, or hours. The monitoring and the inhibition then to be adjusted is preferably effected under computer control.

If the temperature increase falls below 40 K, the content of oligomers in the feed to at least one reactor of the at least one reaction stage is reset to the value which existed before the adjustment, i.e. before the inhibition.

The content of oligomers in the feed can be adjusted by the separation efficiency of the distillation column(s), i.e. if fewer oligomers are separated off in the distillation, more oligomers can be fed into the reactor or reactors in order to contribute to the inhibition. Preferably, the oligomer content is adjusted by boiling oligomers in the distillate (residual oligomerizate) of the distillation column(s) and then returning the mixture "contaminated" with oligomers back to the reactor(s). This corresponds to an artificial deterioration in the purity of the recycled residual oligomerizate.

The following explanations relate to the method according to the invention for inhibition and the method according to the invention for oligomerization respectively.

In the context of the present invention, the term "reaction stage" means a plant section comprising one or more reactor(s) and one or more distillation column(s) downstream of the reactor. In a preferred embodiment, only one distillation column is present per reaction stage. In the distillation columns, the oligomers formed are separated from the oligomerizate (which corresponds to the output stream from the reactor), which in addition to the oligomers also comprises alkanes and unreacted olefins. The efficiency of the separation can also be adjusted by means of the distillation columns in order to be able to feed the amount of oligomers required to the reactor or reactors in each case for sufficient inhibition. Typical process-engineering units which can be incorporated in the reaction stages, such as preheaters for the feed, heat exchangers or similar, for example, are not listed separately here but are familiar to those skilled in the art.

The processes according to the invention each comprise at least one reaction stage. However, the particular process can also comprise at least two reaction stages, wherein there are preferably not more than five reaction stages. In a preferred embodiment, the particular method for inhibition or for oligomerization therefore comprises two, three, four or five reaction stages. Each of these reaction stages, independently of one another, comprises one or more reactors and one or more downstream distillation columns in order to separate the oligomers formed from the residual output stream from the reactor, it is also conceivable, however, that one of the reaction stages comprises two or more reactors, whereas in a preceding or subsequent reaction stage only one reactor is present.

When carrying out the process with two or more reaction stages, the oligomers formed in the reactor or in the reactors of the first reaction stage are separated from the residual oligomerizate in the distillation column of the first reaction stage such that the content of oligomers in the feed is at least 1% by weight, based on the total composition of the feed, when the residual oligomerizate is at least partially mixed with fresh feed and is fed to the first reactor of the first reaction stage. The contents can be checked, for example, using gas chromatographic methods. The corresponding residual oligomerizate is partially fed to the, or to one of the, reactor(s) of the same reaction stage and partially to the next reaction stage. The at least partial conveying of the residual oligomerizate to the next reaction stage is naturally not applicable in the last reaction stage. In addition to recycling to the reactor of the same reaction stage and conveying to the next reaction stage, part of the residual oligomerizate can also be removed, for example to prevent inert alkanes from accumulating in the system.

The process for inhibition according to the invention can be carried out very generally as follows, preferably if inhibition of the oligomerization is required: the starting point is the provision of a feed mixture comprising $C_3$- to $C_5$-olefins, preferably $C_4$-olefins. The feed mixture is firstly oligomerized in the at least one reactor of the first reaction stage and the oligomerizate obtained is passed to a distillation column in which the oligomers formed (preferably $C_6$- to $C_{20}$-olefins, particularly preferably $C_8$- to $C_{20}$-olefins) are separated as bottom product from the residual oligomerizate, which comprises at least unreacted olefins and alkanes from the feed mixture and which is obtained as the overhead product. Depending on the reaction stage, the residual oligomerizate is then at least partially passed as a feed stream to the next respective reaction stage and partially recycled to the reactor of the same reaction stage and beforehand combined with fresh feed composed of fresh feed mixture, wherein the oligomer content in the feed to the respective reaction stage is at least 1% by weight, preferably 1% by weight to 10% by weight. In the last reaction stage, the oligomerizate can be partly recycled to the reactor in this or a previous reaction stage and partly discharged from the process. If the residual oligomerizate of the last reaction stage is discharged from the process described here, this can serve as synthetic raw material for further processes (e.g. hydroformylation, C-source for light arc in acetylene production), as combustion gas or as a propellant gas after full hydrogenation to alkanes, as cooking gas and the like.

Olefins employable for the relevant process according to the invention are $C_3$- to $C_5$-olefins, preferably $C_4$-olefins or olefin mixtures based thereon, which may also comprise proportions of analogous alkanes. Suitable olefins include α-olefins, n-olefins and cycloalkenes, preferably n-olefins. In a preferred embodiment, the $C_4$-olefin is n-butene.

The olefins are typically not used as reactants in pure form, but in available technical-grade mixtures. The term feed mixture used in this invention is therefore to be understood as encompassing any type of mixture containing the relevant olefins to be oligomerized in an amount which makes it possible to perform the oligomerization economically. The feed mixtures used in accordance with the invention preferably contain practically no further unsaturated compounds and polyunsaturated compounds such as dienes or acetylene derivatives. It is preferable to employ feed mixtures containing less than 5% by weight, in particular less than 2% by weight, of branched olefins based on the olefin proportion.

Propylene ($C_3$) is produced on a large industrial scale by cracking of naphtha and is a commodity chemical which is readily available. $C_5$-olefins are present in light petroleum fractions from refineries or crackers. Technical mixtures which comprise linear $C_4$-olefins are light petroleum fractions from refineries, $C_4$-fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the $C_4$-fraction of a steam cracker. Butadiene is removed in the first step here. This is accomplished either by extraction (distillation) of the butadiene or by selective hydrogenation thereof. In both cases a virtually butadiene-free $C_4$-cut is obtained, the so-called raffinate 1. In the second step, isobutene is removed from the $C_4$-stream, for example by production of MTBE by reaction with methanol. The now isobutene-free and butadiene-free $C_4$-cut, the so-called raffinate II, contains the linear butenes and any butanes. If at least some of the 1-butene obtained is removed therefrom, the so-called raffinate III is obtained.

In a preferred embodiment in the respective process according to the invention, $C_4$-olefin-containing streams are supplied as feed mixture. Suitable substance streams containing $C_4$-olefin are in particular raffinate I, raffinate II and raffinate III.

All reactors known to those skilled in the art can be used as reactor for the respective reaction stages which are suitable for oligomerization, for example tubular reactors, tube bundle reactors, settler-riser reactors, slurry reactors. Preference is given to tubular reactors and/or tube bundle reactors. If a reaction stage has two or more reactors, the reactors can be the same or different from one another. The reactors in a reaction stage may also vary in their construction or their configuration. The first reactor in a reaction stage may have, for example, a larger volume than the subsequent reactor in the same reaction stage. It is also possible that the reactors in the individual reaction stages, provided there are two or more reaction stages, are the same or different from one another. It is also possible here that the reactors in the individual reaction stages are different in their construction or their configuration. The reactor in the first reaction stage may have, for example, a larger volume than one or all reactors in the downstream reaction stages.

The one reactor or the reactors of the individual reaction stages each comprise a heterogeneous oligomerization catalyst for carrying out the oligomerization. The heterogeneous oligomerization catalyst in this case is particularly in the form of granules, art extrudate or in tablet form.

The heterogeneous oligomerization catalysts in the individual reactors of the reaction stages can each be selected independently of one another from transition metal-containing oligomerization catalysts. The transition metals or the appropriate transition metal compounds used are preferably arranged on a support material, containing aluminium oxide, silicon dioxide or aluminosilicate, preferably an aluminosilicate support material.

Compounds of nickel, cobalt, chromium, titanium and tantalum are particularly suitable as transition metal compounds for the oligomerization catalysts used according to the invention. Preference is given to nickel and cobalt compounds, particular preference being given to nickel compounds.

In a preferred embodiment, the oligomerization catalyst according to the invention comprises a nickel compound, preferably nickel oxide, and a support material comprising or consisting of aluminium oxide, silicon dioxide or aluminosilicate, preferably aluminosilicate, can be used. The support material is preferably an amorphous mesoporous aluminosilicate, a crystalline microporous aluminosilicate or an aluminosilicate which has amorphous and crystalline phases. In the context of the present invention "amorphous" is to be understood as meaning the property of a solid which results from the fact that the solid has no crystal structure, i.e. no long-range order. In the context of the present invention, however, it cannot be ruled out that the amorphous aluminosilicate has small crystalline domains.

Further preferred in accordance with the invention, the oligomerization catalyst has a composition of 15% to 40% by weight, preferably 15% to 30% by weight NiO, 5% to 30% by weight $Al_2O_3$, 55% to 80% by weight $SiO_2$ and 0.01% to 2.5% by weight, preferably 0.05% to 2% by weight, of an alkali metal oxide, preferably sodium oxide. The figures are based on a total composition of 100% by weight. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition.

The oligomerization catalyst preferably has a specific surface area (calculated according to BET) of 150 to 700 $m^2/g$, more preferably 190 to 600 $m^2/g$, particularly preferably 220 to 550 $m^2/g$. The BET surface area is measured by nitrogen physisorption according to DIN ISO 9277 (2014-01 version).

If there are two or more reactors in one reaction stage or in two or more reaction stages, there are naturally also two or more oligomerization catalysts. The oligomerization catalysts present in the individual reactors in the reaction stages may be selected in each case independently of one another from the aforementioned substances. The individual oligomerization catalysts in the reactors are not always exactly identical here, but differ from each other in the composition, possibly only to a limited extent. This is also due to the fact that even if each reactor contains a completely identical catalyst composition at the time when the process according to the invention is first started up, this composition changes during operation over time as a result of widely varying effects over the years.

An oligomerization catalyst can be produced by the known processes of impregnation, wherein the support material is charged with a solution of a transition metal compound, especially a nickel compound, and is then calcined, or coprecipitation in which the entire catalyst composition is precipitated from a single, mostly aqueous solution. The oligomerization catalyst can also be produced by other processes familiar to those skilled in the art.

The oligomerization can be carried out in each of the reaction stages present at a temperature in the range of 50 to 200° C., preferably 60 to 180° C., preferably in the range of 60 to 130° C. In accordance with the invention, the temperature rise in the reactor can be a maximum of 40 K. The temperature rise is defined as the difference between the temperature of the reactor discharge and the temperature of the reactor feed (T in the reactor discharge−T in the reactor feed). The pressure of each of the reaction stages present can be from 10 to 70 bar, preferably 20 to 55 bar. In a preferred embodiment of the present invention, the oligomerization is carried out in each reaction stage in the liquid phase. If the oligomerization is to be carried out in the liquid phase the parameters pressure and temperature must to this end be chosen such that the reactant stream (the employed olefins or olefin mixtures) is in the liquid phase.

The weight-based space velocities (reactant mass per unit catalyst mass per unit time; weight hourly space velocity (WHSV)) are in the range between 1 g of reactant per g of catalyst and per h (=1 h$^{-1}$) and 190 h$^{-1}$, preferably between 2 h$^{-1}$ and 35 h$^{-1}$, particularly preferably between 3 h$^{-1}$ and 25 h$^{-1}$.

The linearity of an oligomerization product or of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a $C_8$ fraction. The lower the ISO index, the more linear the construction of the molecules in the respective fraction. The ISO index is calculated according to the following general formula, wherein the proportion of the individual dimer fractions refers to the total dimer fraction:

$$\frac{\left(\begin{array}{c}\text{single-branched dimers (\% by weight)} + \\ 2 \times \text{double-branched dimers (\% by weight)}\end{array}\right)}{100}$$

Accordingly, a dimer mixture having an ISO index of 1.0 has an average of exactly 1 methyl branch per dimeric molecule.

The ISO index of the product from the oligomerization process according to the invention is preferably 0.8 to 1.2, more preferably 0.8 to 1.15.

The oligomers produced by the process according to the invention are utilized inter alia for producing aldehydes, alcohols and carboxylic acids. Thus, for example the dimerizate of linear butenes affords a nonanal mixture by hydroformylation. This provides either the corresponding carboxylic acids by oxidation or a $C_9$-alcohol mixture by hydrogenation. The $C_9$-acid mixture may be used for producing lubricants or siccatives. The $C_9$-alcohol mixture is a precursor for the production of plasticizers, particularly dinonyl phthalates, or DINCH.

EXAMPLES

Example 1 (Inventive)

The oligomerization was reworked in a substantially isothermal tubular reactor with the following dimensions: length 2.0 m, internal diameter 6 mm. The reactor was suspended in a thermostat for thermostatting. The heat carrier used was the Marlotherm product from Sasol. The catalyst used was 12.6 g of a material which had been prepared in accordance with example 1 of WO2011/000697A1 and had been post-treated in accordance with example 4 of the same publication.

The reaction was carried out at an absolute pressure of 30 bar and a temperature of 100° C. in the liquid phase. 118.5 g/h of a $C_4$-hydrocarbon mixture containing the following components were used as fresh feed to the reactor:
1-butene 22.2% by weight
2-butene 57.9% by weight
isobutene 0.6% by weight
butanes 18.2% by weight
$C_8$-olefins 1.1% by weight A conversion of $C_4$-olefins of 41.1% was achieved, the following oligomerizate distribution being achieved in the reactor discharge:
$C_8$-olefins 83.9%
$C_{12}$-olefins 12.4%
$C_{16+}$-olefins 3.8%

This corresponds to a product amount of 32.0 g/h of $C_8$-olefins and a total oligomer amount of 38.5 g/h.

Example 2 (Inventive)

The oligomerization was reworked in a substantially isothermal tubular reactor with the following dimensions: length 2.0 m, internal diameter 6 mm. The reactor was suspended in a thermostat for thermostatting. The heat carrier used was the Marlotherm product from Sasol. The catalyst used was 12.6 g of a material which had been prepared in accordance with example 1 of WO2011/000697A1 and had been post-treated in accordance with example 4 of the same publication.

The reaction was carried out at an absolute pressure of 30 bar and a temperature of 100° C. in the liquid phase. 118.5 g/h of a $C_4$-hydrocarbon mixture containing the following components were used as fresh feed to the reactor:
1-butene 21.4% by weight
2-butene 57.7% by weight
isobutene 0.5% by weight
butanes 17.3% by weight
$C_8$-olefins 3.1% by weight A conversion of $C_4$-olefins of 38.0% was achieved, the following oligomerizate distribution being achieved in the reactor discharge:
$C_8$-olefins 83.4%
$C_{12}$-olefins 13.0%
$C_{16+}$-olefins 3.6%

This corresponds to a product amount of 29.6 g/h of $C_8$-olefins and a total oligomer amount of 35.6 g/h.

Example 3 (Non-Inventive)

The oligomerization was reworked in a substantially isothermal tubular reactor with the following dimensions: length 2.0 m, internal diameter 6 mm. The reactor was suspended in a thermostat for thermostatting. The heat carrier used was the Marlotherm product from Sasol. The catalyst used was 12.6 g of a material which had been prepared in accordance with example 1 of WO2011/000697A1 and had been post-treated in accordance with example 4 of the same publication.

The reaction was carried out at an absolute pressure of 30 bar and a temperature of 80° C. in the liquid phase. 1 kg/h of a $C_4$-hydrocarbon mixture containing the following components was used as fresh feed to the reactor:
- 1-butene 22.7% by weight
- 2-butene 58.4% by weight
- isobutene 0.7% by weight
- butanes 18.1% by weight
- $C_8$-olefins 0.1% by weight A conversion of $C_4$-olefins of 43.9% was achieved, the following oligomerizate distribution being achieved in the reactor discharge:
- $C_8$-olefins 83.9%
- $C_{12}$-olefins 12.5%
- $C_{16+}$-olefins 3.7%

This corresponds to a product amount of 34.4 g/h of $C_8$-olefins and a total oligomer amount of 41.3 g/h.

Example 4 (Non-Inventive)

The oligomerization was reworked in a substantially adiabatically operated tubular reactor without thermostatting with the following dimensions: length 2.0 m, internal diameter 20.5 mm. The catalyst used was 300 g of a material which had been prepared in accordance with example 1 of WO2011/000697A1 and post-treated in accordance with example 4 of the same publication.

The reaction was carried out at an absolute pressure of 30 bar and a reactor feed temperature of 90° C. in the liquid phase. 1.75 kg/h of a $C_4$-hydrocarbon mixture containing the following components was used as fresh feed to the reactor:
- 1-butene 35.8% by weight
- 2-butene 42.4% by weight
- isobutene 0.9% by weight
- butanes 20.9% by weight
- $C_8$-olefins 0.0% by weight A conversion of $C_4$-olefins of 31.7% was achieved, the following oligomerizate distribution being achieved in the reactor discharge:
- $C_8$-olefins 85.1%
- $C_{12}$-olefins 12.6%
- $C_{16+}$-olefins 2.3%

The maximum temperature of the reactor discharge was 130° C.

Example 5 (Non-Inventive)

The conditions and the reactor corresponded to those of example 4. A $C_4$ mixture was used which had the following composition:
- 1-butene 36.0% by weight
- 2-butene 43.8% by weight
- isobutene 0.7% by weight
- butanes 19.3% by weight
- $C_8$-olefins 0.2% by weight (corresponds to 3.5 g/h)

A conversion of $C_4$-olefins of 31.7% was achieved, the following oligomerizate distribution being achieved in the reactor discharge:
- $C_8$-olefins 85.0%
- $C_{12}$-olefins 12.6%
- $C_{16+}$-olefins 2.4%

The maximum temperature of the reactor discharge was 131° C., No drop in conversion could be found compared to example 4. The temperature increase is furthermore >40 K.

Example 6 (Non-Inventive)

The conditions and the reactor corresponded to those of example 4. A $C_4$ mixture was used which had the following composition:
- 1-butene 36.1% by weight
- 2-butene 44.1% by weight
- isobutene 1.2% by weight
- butanes 18.0% by weight
- $C_8$-olefins 0.4% by weight (corresponds to 7 g/h)

A conversion of $C_4$-olefins of 30.1% was achieved, the following oligomerizate distribution being achieved in the reactor discharge:
- $C_8$-olefins 85.0%
- $C_{12}$-olefins 12.6%
- $C_{16+}$-olefins 2.4%

The maximum temperature of the reactor discharge was 128° C. The temperature increase fell only slightly below a temperature increase of 40 K and the conversion declined only slightly.

Example 8 (Inventive)

The oligomerization was reworked in a substantially adiabatically operated tubular reactor with the following dimensions: length 2.0 m, internal diameter 20.5 mm. The catalyst used was 300 g of a material which had been prepared in accordance with example 1 of WO2011/000697A1 and post-treated in accordance with example 4 of the same publication.

The reaction was carried out at an absolute pressure of 30 bar and a temperature of the reactor feed of 75° C. in the liquid phase. 1.8 kg/h of a $C_4$-hydrocarbon mixture was used comprising the following components as fresh feed to the reactor:
- 1-butene 42.5% by weight
- 2-butene 11.8% by weight
- isobutene 0.1% by weight
- butanes 45.2% by weight
- $C_8$-olefins 0.0% by weight A conversion of $C_4$-olefins of 26.3% was achieved, the following oligomerizate distribution being achieved in the reactor discharge:
- $C_8$-olefins 87.1%
- $C_{12}$-olefins 12.1%
- $C_{16+}$-olefins 0.8%

The maximum temperature of the reactor discharge was 120° C. This corresponds to a temperature increase of 45 K.

It was started with the $C_8$-metering in of 1.1% by weight in addition to the $C_4$-feed. Consequently, 20 g/h $C_8$ were metered in. Inhibition occurred immediately. The metered addition was carried out until the temperature increase had fallen again below the threshold value of 40K. At this time point, a conversion of 20.7% was achieved, the following oligomerizate distribution being achieved in the reactor discharge:

$C_8$-olefins 89.2%
$C_{12}$-olefins 9.9%
$C_{16+}$-olefins 0.9%.

It could be shown that an increase in the $C_8$-olefin content in the feed to the reactor by more than 1% by weight leads to a reduction in the conversion and also the total oligomerizate, which means the oligomerization reaction can be effectively and intentionally inhibited.

The invention claimed is:

1. A process for the specific inhibition of oligomerization of $C_3$- to $C_5$-olefins, comprising:
    oligomerizing a feed mixture comprising the $C_3$- to $C_5$-olefins in the presence of a heterogeneous oligomerization catalyst in at least one reaction stage, the at least one reaction stage in each case comprising:
    at least one reactor in which the oligomerization of the $C_3$- to $C_5$-olefins is carried out to form an oligomerizate, and
    at least one distillation column in which the oligomers formed in the oligomerization are at least partially separated from a residual oligomerizate,
    wherein the oligomerization is inhibited by the fact that a content of oligomers in the feed to the at least one reactor of the at least one reaction stage, which comprises recycled residual oligomerizate and a fresh feed of the feed mixture, is at least 1% by weight, based on a total composition of the feed,
    with the proviso that the inhibition is carried out only when a predetermined value of a process or plant parameter is exceeded, which indicates that the reaction rate of the oligomerization exceeds threshold, at least locally, in one or more reactors, based on the respective reactor.

2. The process according to claim 1, wherein the content of oligomers in the feed to at least one reactor of the at least one reaction stage is 1% by weight to 10% by weight, based on the total composition of the feed.

3. The process according to claim 1, wherein the heterogeneous oligomerization catalyst is a transition metal-containing oligomerization catalyst comprising:
    a transition metal compound, and
    a support material.

4. The process according to claim 3, wherein the heterogeneous oligomerization catalyst has a composition of:
    15 to 40% by weight NiO,
    5 to 30% by weight $Al_2O_3$,
    55 to 80% by weight $SiO_2$, and
    0.01 to 2.5% by weight of an alkali metal oxide.

5. The process according to claim 3, wherein the support material s aluminosilicate support material.

6. The process according to claim 1, wherein the oligomerization in each of the reaction stages present is carried out at a temperature in a range of 50 to 200° C.

7. The process according to claim 6, wherein the temperature is in the range of 60 to 130° C.

8. The process according to claim 1, wherein a pressure in the oligomerization in each of the reaction stages present is from 10 to 70 bar.

9. The process according to claim 8, wherein the pressure is from 20 to 55 bar.

10. The process according to claim 1, wherein $C_4$-olefins are used in process.

11. The process according to claim 1, wherein the process or plant parameter, which indicates that the reaction rate exceeds threshold, is a temperature increase, an absolute or local temperature in the reactor, a concentration of products and/or by-products, a pressure increase due to an increasing vapour pressure at elevated temperature, and/or a pressure loss across the reactor.

12. A process for oligomerization of $C_3$- to $C_5$-olefins, comprising:
    oligomerizing a feed mixture comprising $C_3$- to $C_5$-olefins in the presence of an oligomerization catalyst in at least one reaction stage to obtain an oligomerizate,
    separating the oligomers formed at least partially in at least one downstream distillation column from a residual oligomerizate, wherein the residual oligomerizate is at least partially recycled to the at least one reactor,
    wherein the reaction stage or at least one of the reaction stages comprises at least one adiabatically operated reactor,
    wherein, in the adiabatically operated reactor, a temperature increase, the difference between the temperature of the reactor discharge and the temperature of the reactor feed, is at least temporarily 40 K or more, and
    monitoring the temperature increase, and
    when the temperature increase exceeds a threshold value of 40 K, the oligomer content in the feed to the at least one reactor of the at least one reaction stage, which comprises recycled residual oligomerizate and a fresh feed of the feed mixture, is adjusted to 1% by weight to 10% by weight, based on a total composition of the feed.

13. The process according to claim 12, wherein the heterogeneous oligomerization catalyst is a transition metal-containing oligomerization catalyst comprising
    a transition metal compound, and
    a support material.

14. The process according to claim 13, wherein the heterogeneous oligomerization catalyst has a composition of
    15 to 40% by weight NiO,
    5 to 30% by weight $Al_2O_3$,
    55 to 80% by weight $SiO_2$, and
    0.01 to 2.5% by weight of an alkali metal oxide.

15. The process according to claim 13, wherein the support material aluminosilicate support material.

16. The process according to claim 12, wherein the oligomerization in each of the reaction stages present is carried out at a temperature in a range of 50 to 200° C.

17. The process according to claim 16, wherein the temperature is in the range of 60 to 130° C.

18. The process according to claim 12, wherein a pressure in the oligomerization in each of the reaction stages present is from 10 to 70 bar.

19. The process according to claim 18, wherein the pressure is from 20 to 55 bar.

20. The process according to claim 12, wherein $C_4$-olefins are used in the process.

* * * * *

UNITED STATES PATENT AND TRADEMARK OFFICE
CERTIFICATE OF CORRECTION

| | |
|---|---|
| PATENT NO. | : 11,254,625 B2 |
| APPLICATION NO. | : 15/929599 |
| DATED | : February 22, 2022 |
| INVENTOR(S) | : Stephan Peitz et al. |

It is certified that error appears in the above-identified patent and that said Letters Patent is hereby corrected as shown below:

On the Title Page

A reference under Item (56) the Other Publications section at Column 2, Line 1, currently reads:
"U.S. Appl. No. 15/929,599, filed May 12, 2020, Stochniol et al."
Should read:
--U.S. Appl. No. 15/929,604, filed May 12, 2020, Stochniol et al.--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*